(12) United States Patent
Proksa

(10) Patent No.: US 9,980,686 B2
(45) Date of Patent: May 29, 2018

(54) HYBRID (SPECTRAL/NON-SPECTRAL) IMAGING DETECTOR ARRAY AND CORRESPONDING PROCESSING ELECTRONICS

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 25 days.

(21) Appl. No.: 14/905,890

(22) PCT Filed: Jul. 4, 2014

(86) PCT No.: PCT/IB2014/062846
§ 371 (c)(1),
(2) Date: Jan. 18, 2016

(87) PCT Pub. No.: WO2015/011587
PCT Pub. Date: Jan. 29, 2015

(65) Prior Publication Data
US 2016/0157795 A1    Jun. 9, 2016

Related U.S. Application Data

(60) Provisional application No. 61/857,258, filed on Jul. 23, 2013.

(51) Int. Cl.
*A61B 6/03*    (2006.01)
*A61B 6/00*    (2006.01)
(Continued)

(52) U.S. Cl.
CPC ............ *A61B 6/4241* (2013.01); *A61B 6/032* (2013.01); *A61B 6/4233* (2013.01); *A61B 6/482* (2013.01);
(Continued)

(58) Field of Classification Search
CPC ..... A61B 6/4241; A61B 6/032; A61B 6/4233; A61B 6/482; A61B 6/5205; A61B 6/5235; G01T 1/2985
See application file for complete search history.

(56) References Cited

U.S. PATENT DOCUMENTS 7,450,683 B2    11/2008    Tkaczyk
7,956,332 B2    6/2011    Burr
(Continued)

OTHER PUBLICATIONS

Hao Gao, et al., "Papers; Multi-energy CT based on a prior rank, intensity and sparsity model (PRISM)", Inverse Problems, Institute of Physics Publishing, vol. 27, No. 11, Oct. 25, 2011.

*Primary Examiner* — Casey Bryant

(57) ABSTRACT

An imaging system (100) includes a detector array (110) that detects radiation traversing an examination region. The detector array includes at least a set of non-spectral detectors (112) that detects a first sub-portion of the radiation traversing the examination region and generates first signals indicative thereof. The detector array further includes at least a set of spectral detectors (114) that detects a second sub-portion of the radiation traversing the examination region and generates second signals indicative thereof. The imaging system further includes a reconstructor (120) that processes the first and second signals, generating volumetric image data.

7 Claims, 4 Drawing Sheets

Figure 1:
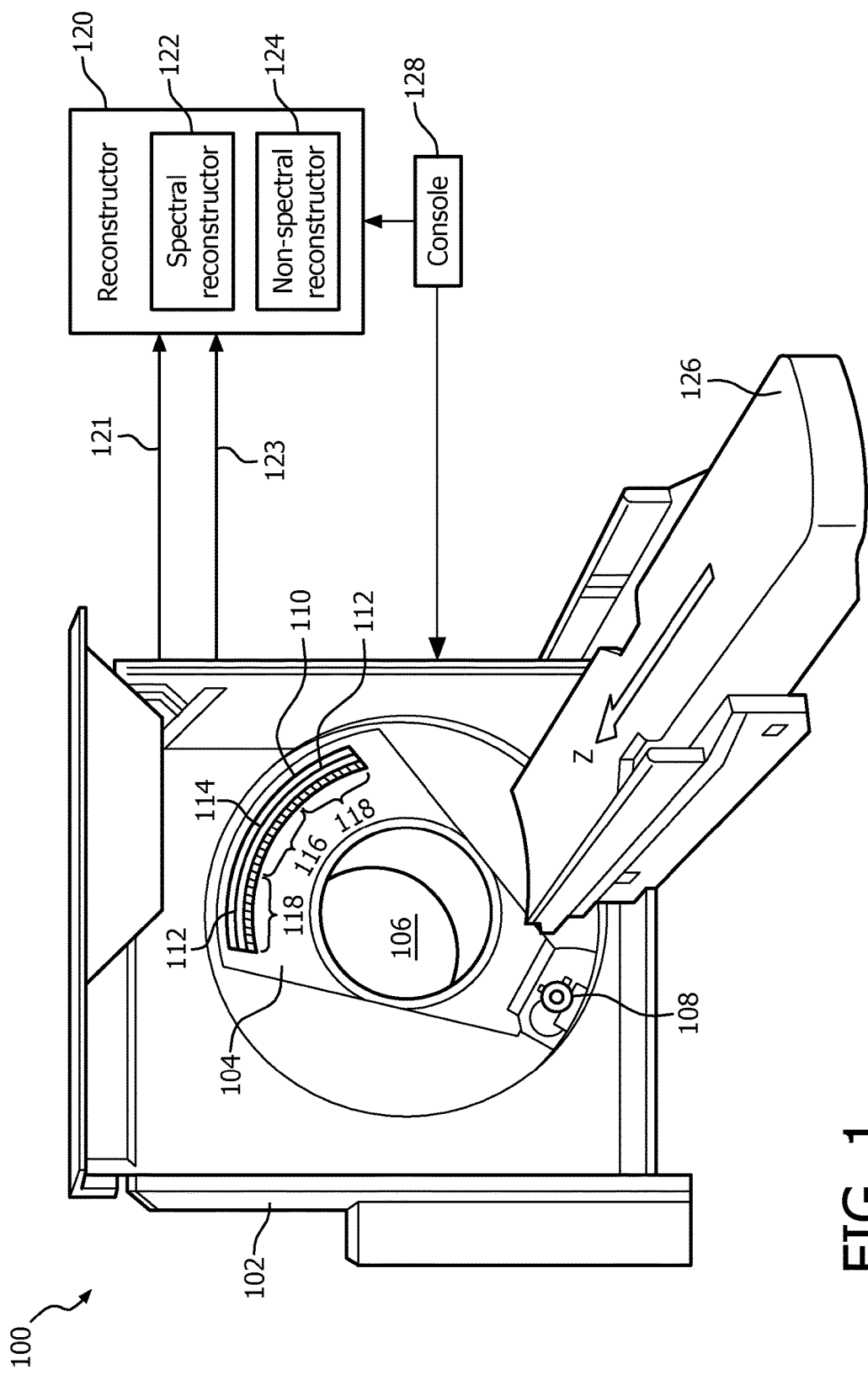

(51) Int. Cl.
  *G01T 1/29* (2006.01)
  *G06T 11/00* (2006.01)
(52) U.S. Cl.
  CPC .......... *A61B 6/5205* (2013.01); *A61B 6/5235* (2013.01); *G01T 1/2985* (2013.01); *G06T 11/003* (2013.01); *G06T 11/006* (2013.01); *A61B 6/4064* (2013.01); *A61B 6/4078* (2013.01); *A61B 6/4085* (2013.01); *A61B 6/5258* (2013.01); *G06T 2211/408* (2013.01); *G06T 2211/424* (2013.01)

(56) References Cited

U.S. PATENT DOCUMENTS

| | | | |
|---|---|---|---|
| 7,968,853 B2 * | 6/2011 | Altman | A61B 6/032 250/366 |
| 8,442,184 B2 | 5/2013 | Forthmann | |
| 2006/0027755 A1 | 2/2006 | Tai | |
| 2007/0147574 A1 * | 6/2007 | Bernard De Man | A61B 6/032 378/4 |
| 2007/0147696 A1 * | 6/2007 | Karl | G06T 11/005 382/254 |
| 2008/0210877 A1 * | 9/2008 | Altman | A61B 6/032 250/366 |

* cited by examiner

HYBRID (SPECTRAL/NON-SPECTRAL) IMAGING DETECTOR ARRAY AND CORRESPONDING PROCESSING ELECTRONICS

CROSS REFERENCE TO RELATED APPLICATIONS

This application is the U.S. National Phase application under 35 U.S.C. § 371 of International Application No. PCT/IB2014/062846, filed Jul. 4, 2014, published as WO 2015/011587 on Jan. 29, 2015, which claims the benefit of U.S. Provisional Patent Application No. 61/857,258 filed Jul. 23, 2013. These applications are hereby incorporated by reference herein.

The following generally relates to imaging and more particularly to a hybrid (spectral/non-spectral) imaging detector array and corresponding processing electronics, and is described with particular application to computed tomography (CT). However, the following is also amenable to other imaging modalities.

A non-spectral CT scanner has included an x-ray tube mounted on a rotatable gantry opposite a detector array across an examination region. The rotatable gantry and hence the x-ray tube rotate around the examination region. The x-ray tube is configured to emit radiation that traverses the examination region and is detected by the detector array. The detector array, in response, generates and outputs a signal indicative of the detected radiation. The signal is reconstructed to generate three dimensional volumetric image data. The resulting volumetric image data includes pixels or voxels that typically are represented in terms of gray scale values corresponding to relative radiodensity.

The gray scale values reflect the attenuation characteristics of the scanned subject and/or object, and generally show structure such as anatomical structures within the scanned patient or object. Since the absorption of a photon by a material is dependent on the energy of the photon traversing the material, the detected radiation also includes spectral information, which provides additional information indicative of the elemental or material composition of the scanned material of the subject and/or object. However, the three dimensional volumetric image data does not reflect the spectral characteristics as the signal output by the detector array is proportional to the energy fluence integrated over the energy spectrum.

A spectral CT scanner, on the other hand, captures the above-noted spectral characteristics. A spectral CT scanner has included an energy-resolving detector array such as a detector array with a single detector that includes at least two detector pixels with different spectral sensitivities. An example of a dual-layer or double decker spectral detector is described in U.S. Pat. No. 7,968,853 B2, filed Apr. 10, 2006, and entitled "Double Decker Detector for Spectral CT." In U.S. Pat. No. 7,968,853 B2, the double decker detector includes at least two stacked scintillators with side-mounted photosensors, one photosensor for each of the stacked scintillators, which provides photon energy separation. Unfortunately, such detector a module can be expensive relative to a conventional non-spectral detector having only a single scintillator and a single detector pixel.

Aspects described herein address the above-referenced problems and others.

The following describes an imaging detector array (and an example system in which the array is installed) that includes both spectral detectors and non-spectral detectors. The following also describes a reconstruction approach for reconstructing the detector signals from the spectral and the non-spectral detectors and generating spectral volumetric image data for at least two basis materials. The spectral and the non-spectral detectors can alternatively be processed to generate non-spectral volumetric image data.

In one aspect, an imaging system includes a detector array that detects radiation traversing an examination region. The detector array includes at least a set of non-spectral detectors that detects a first sub-portion of the radiation traversing the examination region and generates first signals indicative thereof. The detector array further includes at least a set of spectral detectors that detects a second sub-portion of the radiation traversing the examination region and generates second signals indicative thereof. The imaging system further includes a reconstructor that processes the first and second signals, generating volumetric image data.

In another aspect, a method includes obtaining first signals indicative of radiation detected by a non-spectral detector of an imaging system. The method further includes obtaining second signals indicative of radiation detected by a spectral detector of the imaging system. The method further includes reconstructing the first and second signals, thereby generating at least spectral volumetric image data.

In another aspect, a hybrid imaging detector array includes a plurality of spectral detectors located in a center region of the array and a plurality of non-spectral detectors located at at least one outer region of the array.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system including a hybrid detector array with spectral and non-spectral detectors.

Figure 2:
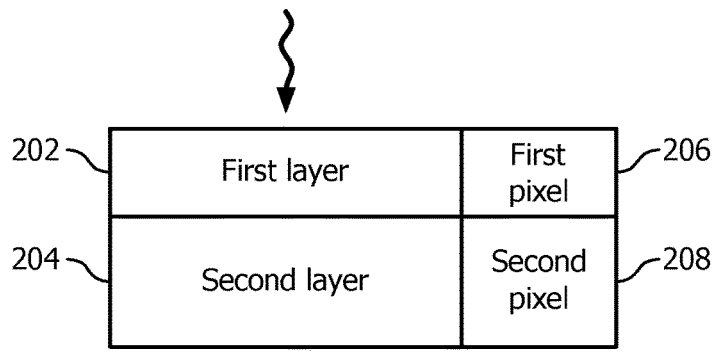

FIG. 2 schematically illustrates an example vertically stacked dual scintillator/dual detector pixel spectral detector with side-mounted detector pixels.

Figure 3:
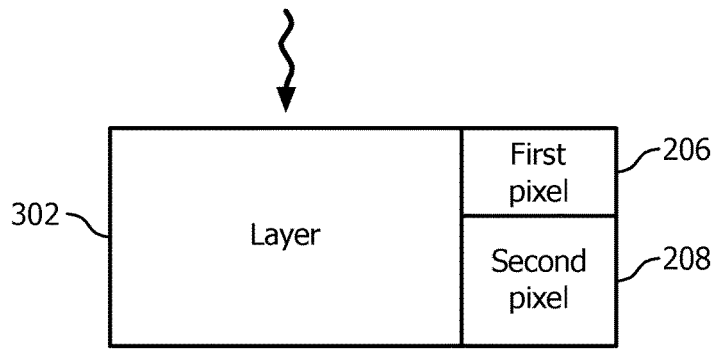

FIG. 3 schematically illustrates an example single scintillator/dual detector pixel spectral detector with side-mounted detector pixels.

Figure 4:
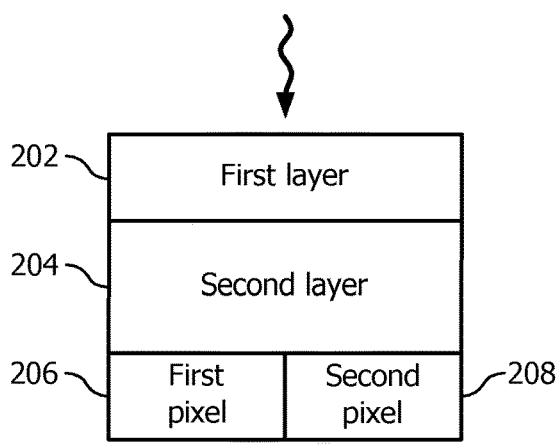

FIG. 4 schematically illustrates an example horizontally arrange dual scintillator/dual detector pixel spectral detector with bottom-mounted detector pixels.

Figure 5:
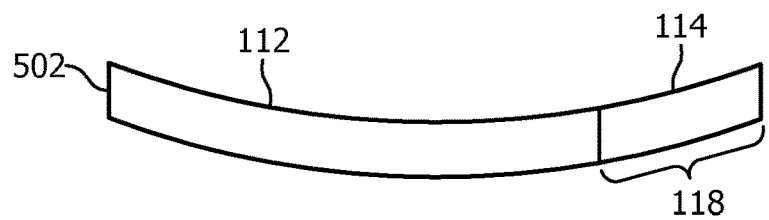

FIG. 5 schematically illustrates alternative example configuration of the hybrid detector array in which non-spectral detectors are only located at one of the end regions of the hybrid detector array.

Figure 6:
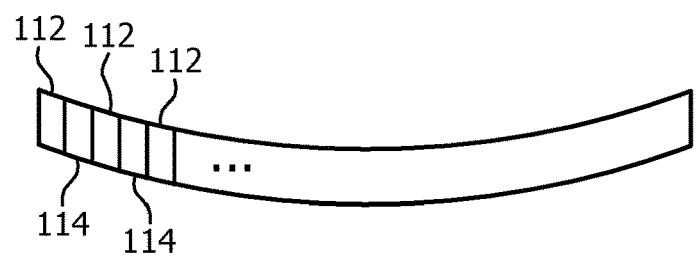

FIG. 6 schematically illustrates alternative example configuration of the hybrid detector array in which non-spectral detector and spectral detectors are interleaved.

Figure 7:
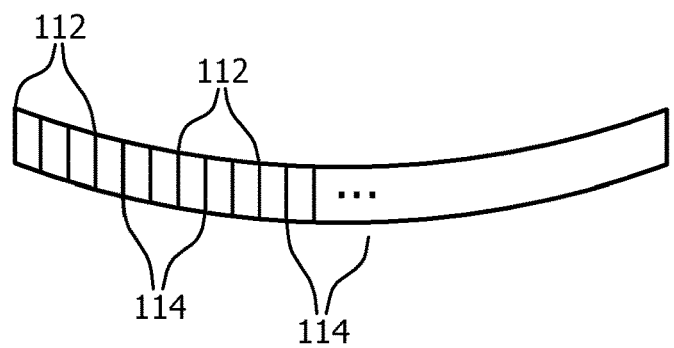

FIG. 7 schematically illustrates alternative example configuration of the hybrid detector array in which groups of non-spectral detector and groups of spectral detectors are interleaved.

Figure 8:
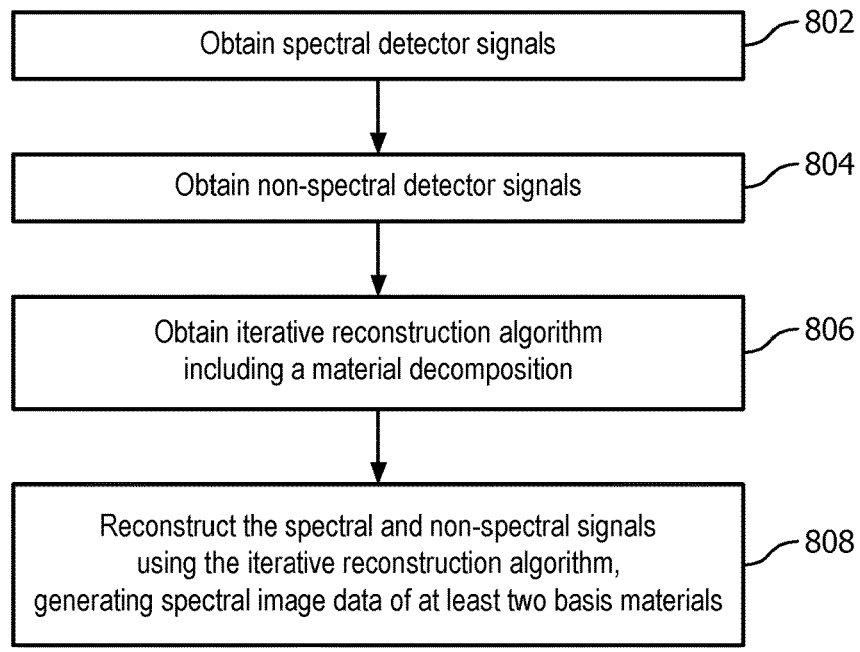

FIG. 8 schematically illustrates an example method for processing detector signals for the embodiments herein, producing spectral image data.

Figure 9:
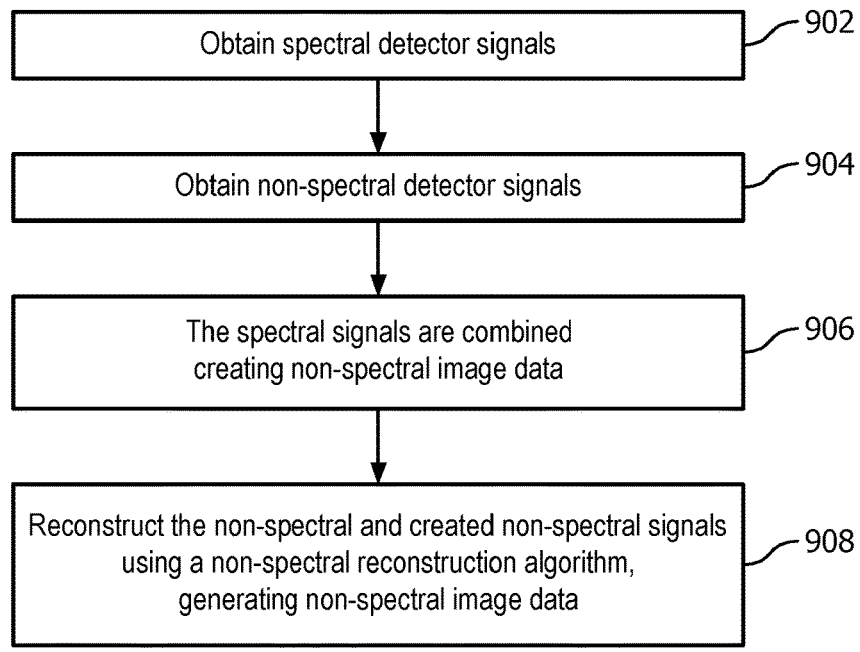

FIG. 9 schematically illustrates an example method for processing detector signals for the embodiments herein, producing non-spectral image data.

The following describes a hybrid imaging detector array, which includes both spectral detectors and non-spectral detectors and a reconstruction approach for reconstructing the detector signals from the spectral and the non-spectral detectors and generating spectral volumetric image data for at least two basis materials and/or non-spectral volumetric image data.

FIG. 1 illustrates an example imaging system 100 such as a computed tomography (CT) system. The imaging system 100 includes a generally stationary gantry 102 and a rotating gantry 104, which is rotatably supported by the stationary gantry 102. The rotating gantry 104 rotates around an examination region 106 about a longitudinal or z-axis.

A radiation source 108, such as an x-ray tube, is supported by the rotating gantry 104 and emits poly-energetic/chromatic radiation. A collimator (not visible) collimates the radiation beam to produce a generally cone, fan, wedge, cone or otherwise shaped radiation beam that traverses the examination region 106 and the portion of the subject or object disposed therein.

A one or two dimensional radiation sensitive detector array 110 detects radiation that traverse the examination region 106. As described in greater detail below, the radiation sensitive detector array 110 is a hybrid array in that it includes both non-spectral detectors 112 and spectral detectors 114. For explanatory purposes, the illustrated spectral detectors 112 are located in a center region 116 and the non-spectral detectors 114 are located in outer regions 118 of the array 110. Other configurations are described below.

In one instance, a size of the center region 116 corresponds to a field of view of sufficient size to image a human or animal heart, head and/or other anatomy. In another instance, the size of the center region 116 may be larger or smaller. It is to be appreciated that utilizing a combination of the spectral detectors 112 and the non-spectral detectors 114 may reduce overall system cost relative to a configuration which only includes the spectral detectors 112, while providing spectral capabilities.

Generally, the non-spectral detectors 112 can be scintillator/photosensor based detectors in which a single scintillator is optically coupled to a single photosensor. The single scintillator produces optical photons in response to detecting incident x-ray radiation. The optical photons are indicative of the detected x-ray radiation. The photosensor sense the optical photons and generates signals indicative thereof and hence indicative of the detected photons.

The spectral detectors 114 include multiple or a single scintillator layer optically coupled to multiple photosensors. Lower energy photons generally are absorbed in scintillators layers or the portion of a single layer closer to the incident radiation. In contrast, higher energy photons generally are absorbed in scintillators layers or the portion of a single layer farther away from the incident radiation. The output of the respective detectors corresponds to different energy photons. In a variation, at least one of the spectral detectors 114 includes a solid-state spectral detector. For instance, at least one of the spectral detectors 114 can include a direct conversion material such as cadmium telluride (CdTe), cadmium zinc telluride (CdZnTe, or CZT), etc.

A reconstructor 120 reconstructs the signals 121 from the non-spectral detectors 112 and the signals 123 from the spectral detectors 114. The reconstructor 120 includes a spectral reconstructor 122. As described in greater detail below, the spectral reconstructor 122 employs an algorithm that includes material decomposition such as an iterative statistical reconstruction algorithm that maximizes a likelihood that an intermediate image fits the measured data given a noise model and additional constraints.

Such an algorithm requires a forward model of the data acquisition process, estimating what the system 100 theoretically would measure if the intermediate image would be the object scanned. A material decomposition from M energies can produce sets of up to M images. In the case of M=2, this may include photoelectric effect and Compton Effect sets, Iodine and virtual non contrast sets, and/or other sets. In this case, the reconstruction would be over both basis materials.

The reconstructor 120 also includes a non-spectral reconstructor 124. In one instance, the signals 123 from the individual photosensors of the spectral detectors 114 are added together producing a combined signal and the both the combined signal and the signals 121 from the non-spectral detectors are reconstructed. A conventional filtered-back projection (FBP) reconstruction, an iterative reconstruction, and/or other reconstruction can be employed.

A subject support 126 such as a couch supports a subject or an object in the examination region 106. A computer serves as an operator console 128. The console 128 includes a human readable output device such as a monitor or display and an input device such as a keyboard and mouse. Software resident on the console 128 allows the operator to interact with the scanner 100 via a graphical user interface (GUI) or otherwise.

The reconstructor 120 can be implemented by a computer processor (e.g., a cpu, a microprocessor, etc.) executing computer readable instructions stored on computer readable storage medium (which excludes transitory medium) such as physical memory Additionally or alternatively, at least one of the computer readable instructions can be carried by a signal, carrier wave, and/or other transitory medium.

FIGS. 2, 3 and 4 show examples of suitable spectral detectors. Another example of a dual layer spectral detector is described in patent application Ser. No. 11/912,673, filed Oct. 26, 2007, and entitled "Double Decker Detector for Spectral CT," the entirety of which is incorporated herein by reference.

In FIG. 2, first and second scintillator layers 202 and 204 are stacked in a direction of the incident radiation. Absorption of the incident radiation in the scintillator layers 202 and 204 is energy-dependent, with lower energy photons travelling on average a shorter distance through the scintillator array before being absorbed in the first layer 202, and higher energy photons travelling on average a greater distance through the scintillator array before being absorbed in a second layer 204.

The first and second scintillator layers 202 and 204 are respectively optically side-mounted to first and second detector pixels 206 and 208, which have first and second spectral responses tuned to the first or second scintillator layers 202 and 204. In this manner, the spectral detector pixels 206 and 208 have two spectrally different outputs. A light reflective film or coatings can be placed on the sides of the layers 202 and 204 to direct light towards the pixels 206 and 208.

FIG. 3 illustrates a variation of FIG. 2 in which a single scintillator layer 302 is optically side-mounted to the first and second pixels 206 and 208. Likewise, the depth of the absorption is indicative of the energy of the detected radiation. This variation is well suited for applications in which it is desirable to have the same scintillator response for each detector pixel 206 and 208 since the same scintillator layer 302 produces optical photons for both of the pixels 206 and 208.

In FIG. 4, the second scintillator layer 204 is optically coupled on top of the detector pixels 206 and 208. With the configurations of FIGS. 2 and 4, the scintillator layers 202 and 204 can be formed from the same or different emitter materials, and/or the scintillator layers 202 and 204 can have similar or different dimensions, such as similar or different depths in the direction of the incoming radiation. Of course, more scintillator layers and photosensitive pixels can be used in other embodiments.

In FIG. 1, the detector array 110 includes a center region 116 with the spectral detectors 112 and outer regions 118 with the non-spectral detectors 114. FIG. 5 illustrates a variation in which the spectral detectors 112 extend to one beyond the center region 116 (FIG. 1) and all the way to the end 502 of the detector array 110. The non-spectral detectors 114 populate one of the outer regions 118 as discussed in connection with FIG. 1.

FIG. 6 illustrates a variation in which the spectral detectors 112 and the non-spectral detectors 114 are interlaced along a row of detectors such that every other detector is either a spectral detector 112 or a non-spectral detector 114. The same or different pattern can extend to additional rows along the z-axis.

FIG. 7 illustrates a variation in which groups of the spectral detectors 112 and groups of the non-spectral detectors 114 are interlaced along a row of detectors such that every other group includes either a spectral detector 112 or a non-spectral detector 114. The same or different pattern can extend to additional rows along the z-axis.

As discussed above, an iterative reconstruction can be employed by both the non-spectral reconstructor 122 and spectral reconstructor 124. A general formulation of such an algorithm for a non-spectral reconstruction is shown in EQUATIONS 1 and 2:

$$\hat{x} \triangleq \operatorname{argmin}_x(L_{NS}(x)), \quad \text{EQUATION 1:}$$

and $$L_{NS}(x) = L(Ax|y) + \beta \cdot R(x), \quad \text{EQUATION 2:}$$

where L(Ax|y) represents a negative log likelihood term that compares a forward projected image (Ax, where A is a forward projection operator and x is the image) to measured data (y), R(x) represents a roughness penalty term that penalizes noise in the reconstructed image (x), and β represents a regularization term that controls a strength of the penalty. Without the penalty, the algorithm may converge to a noisy image to match the noise present in the data.

Again, the signals from the spectral detectors 114 can be combined to create non-spectral data. In this case, the non-spectral reconstructor 124 can employ the algorithm of EQUATION 1 and/or another algorithm, such as another iterative algorithm, a conventional filtered backprojection algorithm (FBP), and/or other approach.

For a spectral reconstruction, a general formulation is shown in EQUATION 3 and 4:

$$\widehat{B_1}, \widehat{B_2}, \ldots, \widehat{B_N} \triangleq \operatorname{argmin}_{B_1, B_2, \ldots, B_N}(L_S(B_1, B_2, \ldots, B_N)), \quad \text{EQUATION 3:}$$

and $$L_S(B_1, B_2, \ldots, B_N) = L_1(B_1, B_2, \ldots, B_N) + \alpha L_2(B_1, B_2, \ldots, B_N) + \beta R(B_1, B_2, \ldots, B_N), \quad \text{EQUATION 4:}$$

where α is a constant, $B_1, B_2, \ldots B_N$ represents N basis materials, $L_1$ is a negative log likelihood of the projection data obtained for the single layer detectors 112, and $L_2$ a negative log likelihood of the projection data obtained for the multilayer detectors 114. Both data terms ($L_1$ and $L_2$) are defined over all basis material images and reflect the spectral sensitivity and the noise model of the individual detector.

The spectral reconstructor 122 can employ the algorithm of EQUATIONS 3 and 4 to process the signals from the spectral 114 and non-spectral detectors 112, producing spectral imaged data for at least two basis materials.

FIG. 8 illustrates an example method for generating spectral image data in connection with the embodiments herein.

It is to be appreciated that the ordering of the acts of these methods is not limiting. As such, other orderings are contemplated herein. In addition, one or more acts may be omitted and/or one or more additional acts may be included.

At 802, first detector signals from a first set of spectral detectors of an imaging system are obtained.

At 804, second detector signals from a second set of spectral detectors of an imaging system are obtained.

At 806, an iterative statistical reconstruction algorithm that includes a spectral data term and a non-spectral data term is obtained.

At 808, the iterative statistical reconstruction algorithm is employed to reconstruct the first and second signals. The algorithm maximizes a likelihood that an intermediate image fits the measured data given a noise model and a regularization term.

Turning to FIG. 9, an example method for generating non-spectral image data in connection with the embodiments herein is illustrated.

It is to be appreciated that the ordering of the acts of these methods is not limiting. As such, other orderings are contemplated herein. In addition, one or more acts may be omitted and/or one or more additional acts may be included.

At 902, first detector signals from a first set of spectral detectors of an imaging system are obtained.

At 904, second detector signals from a second set of spectral detectors of an imaging system are obtained.

At 906, the second detector signals are combined, thereby creating non-spectral detector signals.

At 908, a non-spectral reconstruction algorithm is utilized to reconstruct the first detector signals and the created non-spectral signals.

The above may be implemented by way of computer readable instructions, encoded or embedded on computer readable storage medium (which excludes transitory medium), which, when executed by a computer processor (s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
   a detector array that detects x-ray radiation traversing an examination region, the detector array, including:
      at least a set of spectral detectors that detect a first sub-portion of the radiation traversing the examination region and generates first signals indicative thereof;
      a first inner region relative to the center of the detector array populated with a first portion of the set of spectral detectors and a first outer region relative to the first inner region populated with a second portion of the set of spectral detectors;

at least a set of non-spectral detectors that detects a second sub-portion of the radiation traversing the examination region and generates second signals indicative thereof; and
a second outer region relative to the first outer region populated with the set of non-spectral detectors; and
a reconstructor that processes the first and second signals, generating volumetric image data, the reconstructor comprising:
a spectral reconstructor that processes the first and second signals with a spectral reconstruction algorithm thereby reconstructing spectral volumetric image data, wherein the spectral reconstruction algorithm is an iterative statistical reconstruction algorithm that includes a material decomposition and a log likelihood reconstruction.

2. The system of claim 1, a spectral detector of the set of spectral detectors, comprising:
at least a single scintillator layer; and
at least two detector pixels, wherein the at least two detector pixels are optically side-mounted to the at least a single scintillator in a direction traverse to incident radiation.

3. The system of claim 1, a spectral detector of the set of spectral detectors, comprising:
at least two scintillator layers stacked one upon another; and
at least two detector pixels wherein each of the at least two detector pixels is respectively optically side-mounted to a different one of the at least two scintillators in a direction traverse to incident radiation.

4. The system of claim 1, a spectral detector of the set of spectral detectors, comprising:
at least two stacked scintillator layers; and
at least two detector pixels, wherein the stack of scintillator layers are disposed over the at least two detector pixels in a direction of incident radiation.

5. The system of claim 1, the reconstructor, further comprising:
a non-spectral reconstructor that combines the first signals, thereby creating non-spectral signals and processes the second signals and the created non-spectral signals with a non-spectral reconstruction algorithm to reconstruct the volumetric image data.

6. The system of claim 1, wherein the spectral reconstruction algorithm includes a data term with a non-spectral data component and a spectral data component and a regularization term, each term being a function of two or more basis material, and the spectral reconstructor maximizes a likelihood that an intermediate image fits a measured data given a noise model and regularization factor.

7. The system of claim 1, wherein the reconstructor is configured to process the first and second signals and generate spectral volumetric image data based on the following:

$$L_S(B_1,B_2,\ldots,B_N)=L_1(B_1,B_2,\ldots,B_N)+\alpha L_2(B_1,B_2,\ldots,B_N)+\beta R(B_1,B_2,\ldots,B_N),$$

where $L_S$ is a negative log likelihood for a spectral reconstruction, R represents a roughness penalty term that penalizes noise in the reconstructed image β represents a regularization term that controls a strength of the penalty, α is a constant, B1, B2, ... BN represents N basis materials, N is a positive integer, L1 is a negative log likelihood of projection data generated by the set of non-spectral detectors, and L2 a negative log likelihood of projection data generated by the set of spectral detectors, wherein L1 and L2 are defined over all basis material images and reflect a spectral sensitivity and a noise model of the detector array.

* * * * *